United States Patent [19]

Watanabe et al.

[11] 3,975,181

[45] Aug. 17, 1976

[54] HERBICIDAL COMPOSITION

[75] Inventors: Shiro Watanabe, Osaka; Keiichi Maruo, Suita; Hiroshi Ono, Shiga, all of Japan

[73] Assignee: Daikin Kogyo Co., Ltd., Osaka, Japan

[22] Filed: Mar. 23, 1973

[21] Appl. No.: 344,450

Related U.S. Application Data

[63] Continuation of Ser. No. 864,560, Oct. 7, 1969, abandoned.

[52] U.S. Cl. .................................... 71/113; 71/65; 71/94; 71/101; 71/84
[51] Int. Cl.² .......................................... A01N 9/24
[58] Field of Search ............... 71/113, 94, 101, 100, 71/106

[56] References Cited
OTHER PUBLICATIONS

Thompson Agricultural Chemicals – Book II Herbicides (1964) pp. 53, 54 – 55.

*Primary Examiner*—Lewis Gotts
*Assistant Examiner*—Catherine L. Mills
*Attorney, Agent, or Firm*—Bierman & Bierman

[57] ABSTRACT

A novel herbicidal composition for combating the undesired vegetation of perennial weeds of Cyperaceae and Gramineae comprising as active ingredients at least one of the herbicidal compounds having contact acute phytotoxicity and at least one of the herbicidal compounds having translocated chronic phytotoxicity and being selected from the group consisting of fluoropropionic acids of the formula:

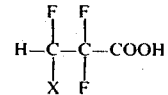

wherein X is fluorine or chlorine, and their salts and amides with an inert carrier.

13 Claims, No Drawings

HERBICIDAL COMPOSITION

This is a continuation of copending application Ser. No. 864,560 filed Oct. 7, 1969, now abandoned.

The present invention relates to a novel herbicidal composition, particularly for combating undesired vegetation of Cyperacease and Gramineae weeds.

Although there have been known a number of herbicidal compounds, none of them are satisfactorily effective in combating undesired vegetation of Cyperaceae and Gramineae weeds, particularly perennial ones, because the subterranean stems of the weeds are widely branched, penetrate deep in the soil and have a very great reproductive power.

For instance, some of the herbicidal compounds having contact acute phytotoxicity such as chlorinated aliphatic acids, quaternary ammonium salts, cyanates and chlorates control the terrestrial stems of the weeds when applied in relatively large amounts but can not kill the subterranean stems, from which the weeds are reproduced.

Further, for instance, some of the herbicidal compounds having translocated chronic phytotoxicity such as 2,2,3,3-tetrafluoropropionic acid and its salts, esters and amides are known to exhibit a herbicidal effect against the said perennial weeds only when applied in comparatively large amounts at the germination period or the very primary stage of growth. In order to expect the significant herbicidal effect on the weeds more grown, it is essential to use the herbicidal compounds in extremely large amounts, which may rather cause chemical injury on useful plants, i.e. crop plants. Moreover, the herbicidal compounds of this kind exert their herbicidal action lately and may require 1 to 6 months until the weeds are withered and killed at ordinary doses.

Surprisingly, it has now been found that the combined use of at least one of herbicidal compounds having contact acute phytotoxicity [hereinafter referred to as "compound(s) A"] with at least one of herbicidal compounds having translocated chronic phytotoxicity [hereinafter referred to as "compound(s) B"] overcomes the drawbacks present in the sole use of those two kinds of herbicidal compounds and exhibits rapidly the excellent herbicidal effect against the perennial weeds of Cyperaceae and Gramineae with prolongation of the effect for a long duration in relatively small amounts. The present invention is based on this finding.

The herbicidal composition of this invention comprises as the active ingredients at least one of the compounds A and at least one of the compounds B.

Examples of the compounds A are as follows: chlorates (e.g. sodium chlorate), quaternary ammonium salts (e.g. paraquat, diquat), chlorinated aliphatic acids (e.g. monochloroacetic acid, dichloroacetic acid, trichloroacetic acid, α,α-dichloropropionic acid, α,α,β-trichloropropionic acid) and their salts and amides, cyanates (e.g. sodium cyanate), xanthogenates (e.g. sodium ethylxanthogenate), etc. The salts may be, for instance, sodium, potassium, calcium, barium, magnesium, zinc, copper, iron, ammonium, dimethylamine or triethanolamine salt. The amides may be, for example, amide, N-lower alkyl amide (e.g. N-methylamide, N-ethylamide) or N,N-di(lower)-alkyl amide (e.g. N,N-dimethylamide, N,N-diethylamide).

The compounds B should be selected from the group consisting of fluoropropionic acids of the formula:

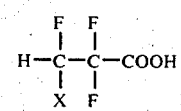

wherein X is fluorine or chlorine, and their salts and amides. The salts may be (e.g. sodium, potassium calcium, barium, magnesium, zinc, copper, iron salts). Examples of the amides are amide, N-lower alkyl amides (e.g. N-methyl, N-ethyl, N-propyl amides) and N,N-di(lower)alkyl amides (e.g. N,N-dimethyl, N,N-diethyl, N,N-dipropyl amides).

The compounds A and B to be incorporated in the novel composition of the invention are preferably employed in a ratio to be determined by the quantities by weight per surface unit in which the relative compounds are to exert their herbicidal action. The quantity by weight for the compounds B is 0.2 to 1.0 kg/10a, preferably 0.25 to 0.5 kg/10a, but for the compounds A it cannot be easily indicated in general because the effective quantity depends on the herbicides or combination of herbicides to be employed, the nature of the broad leaved weeds that are to be combated, and the nature of the cultivated plants and soil to be treated.

The preferred quantities by weight for some of the compounds A are as follows: sodium chlorate, 3 to 10 kg/10a; paraquat, 0.03 to 0.1 kg/10a; diquat, 0.05 to 0.1 kg/10a; α,α-dichloropropionic acid or its salt or amide, 0.5 to 2.0 kg/10a; monochloroacetic acid or its salt or amide, 5 to 10 kg/10a; trichloroacetic acid or its salt or amide, 3 to 5 kg/10a; sodium cyanate, 0.5 to 2.0 kg/10a; sodium ethylxanthogenate, 1.0 to 1.5 kg/10a, etc. Thus, it can be said that the compounds B on the one side and the compounds A on the other side in the novel composition according to the invention are to be employed preferably in a ratio of 0.2-1.0 to 0.03-10. More specifically, the ratios of the compounds B and chlorates, quaternary ammonium salts, halogenated aliphatic acids or their salts or amides, cyanates and xanthogenates as the compounds A may be respectively 0.2-1.0: 3-10, 0.2-1.0: 0.03-0.1, 0.2-1.0: 0.5-10, 0.2-1.0: 0.5-2.0 and 0.2-10.: 1.0-1.5.

The compounds A and B in combination may be applied alone but preferably in the form of a composition, extended with a carrier material or conditioning agent of the kind used and commonly referred to in the art as a herbicidal adjuvant or modifier. Such adjuvants are inert solids, surface active agents and organic liquids. Usually from 1 to 95% by weight of the active ingredients are included in such composition.

Powder formulations can be prepared with inert powders. The formulations thus can be homogeneous powders that either can be used as such, diluted with inert solids to form dusts, or suspended in water for spray application. The powders usually comprise the active ingredients admixed with minor amounts of conditioning agent. Natural clays, either absorptive such as attapulgite or relatively non-absorptive such as china clays, diatomaceous earth, walnut shell flour, redwood, synthetic fine silica, calcium silicate and other inert solid carriers of the kind conventionally employed in powder fungicidal compositions can be used. The active ingredients usually make up from 25 to 90% of these powder compositions. The solids ordinarily should be very finely divided and should have a particle size below 50 microns and preferably below 2 microns. For conversion of the powders to dusts, talc, pyrophyllite, tobacco dust, volcanic ash and other dense, rapid-settling inert solids customarily are used.

Pellet formulations can be also prepared with inert solid carriers as mentioned above in conventional manners. The active ingredients normally make up from 1 to 30% of the formulations. The pellet size is usually from 0.5 to 5 mm.

If the active compounds used are water soluble, they can be sprayed or in any other desired manner applied to an absorption powder, which can then be dried to produce a dry product. Any of the above absorptive materials can be used for the preparation of such products.

Liquid compositions including the active compounds above described can be prepared by admixing the compounds with a suitable liquid diluent medium. The active compounds can be either in solution or in suspension in the liquid medium. Typical of the liquid media commonly employed are kerosene, dimethylformamide, tetrahydrofuran, xylene, alcohols, alkylated naphthalene, glycols and ketones such as diisobutyl ketone or cyclohexanone. The active ingredients usually make up from 0.5 to 50% of these liquid compositions. Some of these compositions are designed to be used as such, and others to be extended with large quantities of water.

Compositions in the form of wettable powders or liquids can also include one or more surface-active agents such as wetting, dispersing or emulsifying agents. Thus mixtures of the above liquids with the active compounds can contain an emulsifying agent to make an emulsifiable oil composition. The surface-active agents cause the compositions of the liquid or dry to disperse or emulsify easily in water to give aqueous sprays.

The surface-active agents employed can be of the anionic, cationic or nonionic type. They include, for example, sodium oleate, sulfonated petroleum oils, alkyl aryl sulfonates, sodium lauryl sulfate, polyethylene oxides, lignin sulfonates, and other surface-active agents.

The weeds of which the germination and growth are markedly controlled by the herbicidal composition of the invention are Cyperaceae such as Cyprus spp. (sedges), Carex spp. (sedges), Eleocharis spp. (spikerush) or the like and Gramineae such as Bromus spp. (brome), Imperata app., (cogon grass), Miscanthus spp. (panthus grass), Sasa spp. (bamboo grass), Sorghum spp. (Johnson grass), Agropyron repens (couch grass), Lolium spp. (ryegrass) or the like.

The herbicidal composition of the invention is normally used as a herbicide for foliage treatment after germination. But, it may be also used in any other period.

The inherent herbicidal action of the compounds A is early exerted whereas that of the compounds B is lately exerted. It is entirely an unobvious result that the combined use of such herbicidal compounds of which the stages for exertion of the herbicidal activity are different each other produces the excellent synergistic action as stated above.

It should be particularly noted that the amount of the compounds A to be employed in the herbicidal composition of the invention is rather preferred to be so small as being insufficient to exert the herbicidal activity by their sole use. It may be also noted that the amount of the compounds B is reduced to ½ - 1/15, compared with the amount in their sole use.

Practical and presently preferred embodiments of the invention are illustratively shown in the following Examples in which parts are by weight.

EXAMPLE 1.

The following materials are mixed up to make a dust:

| Ingredients | Parts |
|---|---|
| Sodium chlorate | 25 |
| Sodium 2,2,3,3-tetrafluoropropionate | 5 |
| Talc | 70 |

EXAMPLE 2.

The following materials are mixed up to make a dust:

| Ingredients | Parts |
|---|---|
| Trichloroacetic acid | 20 |
| 2,2,3,3-Tetrafluoropropionic acid | 2 |
| Bentonite | 78 |

EXAMPLE 3.

The following materials are mixed up to make a dust:

| Ingredients | Parts |
|---|---|
| Sodium $\alpha,\alpha$-dichloropropionate | 12 |
| Sodium 2,2,3,3-tetrafluoropropionate | 2 |
| Talc | 50 |
| Bentonite | 36 |

EXAMPLE 4.

The following materials are mixed up to make a solution:

| Ingredients | Parts |
|---|---|
| Paraquat | 10 |
| Ammonium 2,2,3,3-tetrafluoropropionate | 30 |
| Polyoxyethylenenonylphenyl ether | 10 |
| Sodium ligninsulfonate | 5 |
| Water | 45 |

EXAMPLE 5.

The following materials are mixed up to make a water soluble powder:

| Ingredients | Parts |
|---|---|
| Sodium cyanate | 65 |
| Sodium 2,2,3-trifluoro-3-chloropropionate | 35 |

EXAMPLE 6.

A solution of 7 parts of the active ingredient(s) in 993 parts of water was applied in the middle of June to the area where about 5,000 to 10,000 stocks of Japanese pampas grass (20 stocks per plot; 30 to 35 cm in stock diameter) per ha were growing. The germination rate and the earing rate were determined as follows:

$$\text{Germination rate} = \frac{\text{Germinated stock numbers}}{\text{Tested stock numbers}} \times 100$$

$$\text{Earing rate} = \frac{\text{Eared stock numbers}}{\text{Tested stock numbers}} \times 100$$

The herbicidal effect was also determined as an average of the index numbers of 20 stocks on the basis of the following criteria:

| | |
|---|---|
| Withered | — 4 |
| Markedly controlled in growth and mostly withered later | — 3 |
| Controlled in growth, withered partly and recovered later | — 2 |
| Partly withered but recovered soon and not controlled in growth | — 1 |
| No effect | — 0 |

The results are shown in Table 1.

Table 1

| Active ingredients | | Amount (g/stock) | Application year | | Next year to application | |
|---|---|---|---|---|---|---|
| | | | Herbicidal effect 20 days after application | Earing rate at the end of October (%) | Germination rate at the end of May (%) | Herbicidal effect at the end of August |
| Sodium trichloro-acetate | + Sodium 2,2,3,3-tetrafluoro-propionate | 5.0 + 0.2 | 3.7 | 15 | 0 | 4.0 |
| | | 5.0 + 0.4 | 3.7 | 0 | 0 | 4.0 |
| | | 5.0 + 0.5 | 3.8 | 0 | 0 | 4.0 |
| | | 3.0 + 0.2 | 1.8 | 15 | 5 | 3.8 |
| | | 3.0 + 0.4 | 1.5 | 5 | 0 | 4.0 |
| | | 3.0 + 0.5 | 1.9 | 0 | 0 | 4.0 |
| Sodium chlorate | + Sodium 2,2,3,3-tetrafluoro-propionate | 3.0 + 0.2 | 1.5 | 60 | 10 | 3.3 |
| | | 3.0 + 0.4 | 2.0 | 15 | 0 | 3.5 |
| | | 3.0 + 0.8 | 2.0 | 0 | 0 | 4.0 |
| | | 5.0 + 0.2 | 2.5 | 35 | 5 | 3.5 |
| | | 5.0 + 0.4 | 2.5 | 5 | 0 | 3.7 |
| | | 5.0 + 0.8 | 2.6 | 0 | 0 | 4.0 |
| | | 10.0 + 0.2 | 3.0 | 20 | 0 | 3.7 |
| | | 10.0 + 0.4 | 3.0 | 0 | 0 | 3.8 |
| | | 10.0 + 0.8 | 3.5 | 0 | 0 | 4.0 |
| Sodium α,α-dichloro-propionate | + Sodium 2,2,3,3-tetrafluoro-propionate | 1.0 + 0.2 | 0.5 | 15 | 10 | 3.2 |
| | | 1.0 + 0.5 | 1.8 | 0 | 0 | 4.0 |
| | | 2.0 + 0.2 | 2.2 | 0 | 5 | 3.8 |
| | | 2.0 + 0.5 | 2.3 | 0 | 0 | 4.0 |
| | | 3.0 + 0.2 | 3.7 | 0 | 5 | 4.0 |
| | | 3.0 + 0.5 | 4.0 | 0 | 0 | 4.0 |
| Sodium trichloroacetate | | 3.0 | 1.5 | 100 | 100 | 0.2 |
| | | 6.0 | 3.3 | 100 | 100 | 1.6 |
| | | 9.0 | 4.0 | 75 | 95 | 2.1 |
| Sodium chlorate | | 5.0 | 2.0 | 100 | 100 | 0.5 |
| | | 10.0 | 3.2 | 95 | 100 | 1.0 |
| | | 20.0 | 3.8 | 40 | 85 | 1.0 |
| Sodium 2,2,3,3-tetrafluoropropionate | | 0.2 | 0 | 100 | 30 | 2.5 |
| | | 0.5 | 0.2 | 100 | 5 | 3.3 |
| | | 1.0 | 0.8 | 100 | 0 | 3.8 |
| Sodium trichloroacetate | | 3.0 | 2.9 | 100 | 100 | 1.2 |
| | | 5.0 | 3.7 | 25 | 75 | 1.8 |

EXAMPLE 7.

A solution of 3 parts of the active ingredient(s) in 997 parts of water was applied in the beginning of July by a sprayer to the field where sedge was growing. Observation was made in the beginning of August to determine the herbicidal effect as in Example 6 and also one month and three months after the application for determining the reproduction rate as follows:

$$\text{Reproduction rate} = \frac{\text{Number of stems in treated plot}}{\text{Number of stems in untreated plot}} \times 100$$

The results are shown in Table 2.

Table 2

| Active ingredients | | Amount (kg/10a) | Herbicidal effect in the beginning of August | Reproduction rate after 1 month (%) | Reproduction rate after 3 months (%) |
|---|---|---|---|---|---|
| Sodium mono-chloro-acetate | + Sodium 2,2,3,3-tetrafluoro-propionate | 6.0 + 0.5 | 4.0 | 0 | 0 |
| | | 6.0 + 1.0 | 4.0 | 0 | 0 |
| | | 4.0 + 0.5 | 4.0 | 0 | 0 |
| | | 4.0 + 1.0 | 4.0 | 0 | 0 |
| Sodium 2,2,3,3- | | 1.0 | 0.5 | 100 | 100 |

Table 2-continued

| Active ingredients | Amount (kg/10a) | Herbicidal effect in the beginning of August | Reproduction rate after 1 month (%) | Reproduction rate after 3 months (%) |
| --- | --- | --- | --- | --- |
| tetrafluoropropionate | 2.0 | 1.2 | 100 | 100 |
| Sodium monochloro- | 4.0 | 3.3 | 100 | 100 |
| acetate | 8.0 | 4.0 | 95 | 100 |

EXAMPLE 8.

A solution of 3 parts of the active ingredient(s) in 997 parts of water was applied in the beginning of June to an orange garden where monocotyledonous weeds (dayflower, large crabgrass, yellow netsedge, orchard grass) and dicotyledonous weeds (smartweed, clover) were growing. Two months after the application, the weight of each fresh weed was measured and the remaining rate was calculated according to the following equation:

$$\text{Remaining rate} = \frac{\text{Total weight of fresh weed in treated plot}}{\text{Total weight of fresh weed in untreated plot}} \times 100$$

The results are shown in Table 3:

Table 3

| Active ingredients | | Amount (g/a) | Remaining rate | | | Chemical injury |
| --- | --- | --- | --- | --- | --- | --- |
| | | | Monocotyledonous weeds (%) | Dicotyledonous weeds (%) | Total weeds (%) | |
| Paraquat + | Sodium 2,2,3,3-tetrafluoropropionate | 5 + 30 | 15 | 73 | 47.5 | None |
| | | 5 + 60 | 9.6 | 54 | 34.4 | '' |
| | | 10 + 30 | 0 | 42 | 23.6 | '' |
| | | 10 + 60 | 0 | 38 | 21.3 | '' |
| Sodium cyanate + | Sodium 2,2,3,3-tetrafluoropropionate | 50 + 30 | 15 | 35 | 27.3 | '' |
| | | 50 + 60 | 0 | 12 | 6.7 | '' |
| | | 100 + 30 | 5 | 10 | 7.8 | '' |
| | | 100 + 60 | 0 | 0 | 0 | '' |
| Sodium 2,2,3,3-tetrafluoropropionate | | 50 | 90 | 100 | 95 | '' |
| | | 100 | 83 | 132 | 110 | '' |
| Paraquat | | 10 | 85 | 73 | 78.3 | '' |
| | | 20 | 48 | 51 | 49.8 | '' |
| Sodium cyanate | | 500 | 38 | 56 | 48.3 | '' |
| | | 1000 | 16 | 42 | 30.5 | '' |
| Untreated | | — | 100 (1.8kg/m²) | 100 (2.3kg/m²) | 100 (4.1kg/m²) | '' |

EXAMPLE 9.

A solution of 3 parts of the active ingredient(s) in 997 parts of water was applied in the beginning of July to paths where monocotyledonous weeds (dayflower, cogon grass, large crabgrass, green foxtail, goosegrass) and dicotyledonous weeds (smartweed, clover, fleabane, aster) were growing. Sixty days after the application, the weight of each fresh weed was measured and the remaining rate was calculated as in Example 8. The results are shown in Table 4:

Table 4

| Active ingredients | | Amount (g/a) | Remaining rate | | |
| --- | --- | --- | --- | --- | --- |
| | | | Monocotyledonous weeds (%) | Dicotyledonous weeds (%) | Total weeds (%) |
| Diquat + | Sodium 2,2,3,3-tetrafluoropropionate | 7 + 50 | 21 | 48 | 43 |
| | | 10 + 50 | 12 | 45 | 36 |
| Sodium ethylxanthogenate + | Sodium 2,2,3,3-tetrafluoropropionate | 100 + 50 | 38 | 36 | 37 |
| | | 150 + 50 | 8 | 11 | 10 |
| Sodium 2,2,3,3-tetrafluoropropionate | | 50 | 91 | 100 | 100 |
| | | 100 | 75 | 100 | 100 |
| Diquat | | 10 | 80 | 65 | 70 |
| | | 15 | 48 | 51 | 51 |
| Sodium ethylxanthogenate | | 300 | 75 | 63 | 65 |
| Untreated | | — | 100 | 100 | 100 |

Table 4-continued

| Active ingredients | Amount (g/a) | Remaining rate | | |
|---|---|---|---|---|
| | | Monocotyledonous weeds (%) | Dicotyledonous weeds (%) | Total weeds (%) |
| | | (1100g/m²) | (2800g/m²) | (3900g/m²) |

What is claimed is:

1. A herbicidal composition for combating the undesirable vegetation of perennial weeds of Cyperaceae and Gramineae comprising at least one herbicide selected from the group consisting of monochloroacetic acid, trichloroacetic acid, α,α-dichloropropionic acid and salts and amides thereof, and at least one herbicidal compound selected from the group consisting of fluoropropionic acids of the formula:

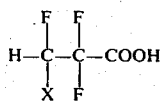

wherein X is fluorine or chlorine, salts of said acids and amides of said acids.

2. The herbicidal composition according to claim 1, wherein the herbicidal compound is 2,2,3,3-tetrafluoropropionic acid, its salt or amide.

3. The herbicidal composition according to claim 1, wherein the ratio by weight of said herbicide to said herbicidal compound is 0.03-10:0.2-1.0.

4. The herbicidal composition according to claim 1, wherein the ratio by weight of said herbicide to said herbicidal compound is 0.03-10:0.25-0.5.

5. The herbicidal composition according to claim 1, wherein said herbicide is monochloroacetic acid, its salt or amide and said herbicidal compound is 2,2,3,3-tetrafluoropropionic acid, its salt or amide; and said herbicide and said herbicidal compound are present in a ratio by weight of 5-10:0.2-1.0.

6. The herbicidal composition according to claim 1, wherein said herbicide is trichloroacetic acid, its salt or amide and said herbicidal compound is 2,2,3,3-tetrafluropropionic acid, its salt or amide; and said herbicide and said herbicidal compound are present in a ratio by weight of 3-5:0.2-1.0.

7. The herbicidal composition according to claim 1, wherein said herbicide is α,α-dichloropropionic acid, its salt or amide and said herbicidal compound is 2,2,3,3-tetrafluoropropionic acid, its salt or amide; and said herbicide and said herbicidal compound are present in a ratio by weight of 0.5-2.0:0.2-1.0.

8. The herbicidal composition according to claim 5 wherein said ratio by weight is 5-10:0.25-0.5.

9. The herbicidal composition according to claim 6, wherein said ratio by weight is 3-5:0.25-0.5.

10. The herbicidal composition according to claim 7 wherein said ratio by weight is 0.5-2.0:0.25-0.5.

11. A method for combating the undesired vegetation of perennial weeds of Cyperaceae and Gramineae which comprises applying to an area wherein a herbicidal effect is desired the herbicidal composition according to claim 7 at a dose of 0.2-1.0 kg of the herbicidal compounds having translocated chronic phytotoxicity per 10 a.

12. The method as claimed in claim 11 wherein said dose is 0.25-0.5 kg.

13. A herbicidal composition as claimed in claim 1, further including an inert carrier.

* * * * *